United States Patent [19]

Holzwarth

[11] Patent Number: 5,024,322

[45] Date of Patent: Jun. 18, 1991

[54] ARMED SUTURE PACKAGE

[75] Inventor: Henry A. Holzwarth, Weston, Conn.

[73] Assignee: United States Surgical Corporation, Norwalk, Conn.

[21] Appl. No.: 515,197

[22] Filed: Apr. 27, 1990

[51] Int. Cl.⁵ .............................................. A61B 17/06
[52] U.S. Cl. ................................................... 206/63.3
[58] Field of Search ....................................... 206/63.3

[56] References Cited

U.S. PATENT DOCUMENTS

| | | | |
|---|---|---|---|
| 2,692,676 | 10/1954 | Grover | 206/63.3 |
| 3,444,994 | 5/1969 | Kaepernik et al. | 206/63.3 |
| 3,985,227 | 10/1976 | Thyen et al. | 206/63.3 |
| 4,089,409 | 5/1978 | Cerwin | 206/63.3 |
| 4,120,395 | 10/1978 | Mandel et al. | 206/63.3 |
| 4,135,623 | 1/1979 | Thyen | 206/63.3 |
| 4,533,041 | 8/1985 | Aday et al. | 206/63.3 |
| 4,615,435 | 10/1986 | Alpern et al. | 206/63.3 |
| 4,884,681 | 12/1989 | Roshdy et al. | 206/63.3 |
| 4,887,710 | 12/1989 | Roshdy et al. | 206/63.3 |
| 4,896,767 | 1/1990 | Pinheiro | 206/63.3 |

Primary Examiner—William I. Price
Attorney, Agent, or Firm—Thomas R. Bremer; Peter G. Dilworth; Rocco S. Barrese

[57] ABSTRACT

A package for storing a quantity of single or double armed sutures is formed from a single sheet of paperboard or other stiff material.

12 Claims, 2 Drawing Sheets

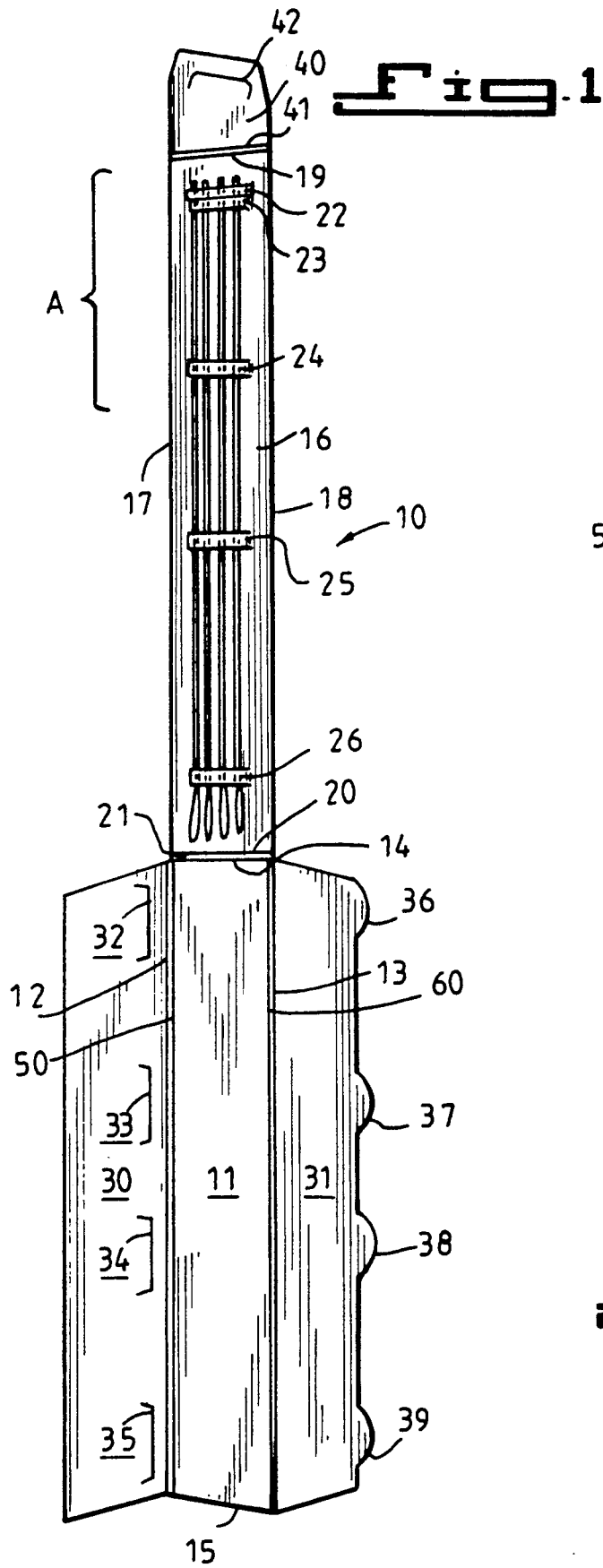
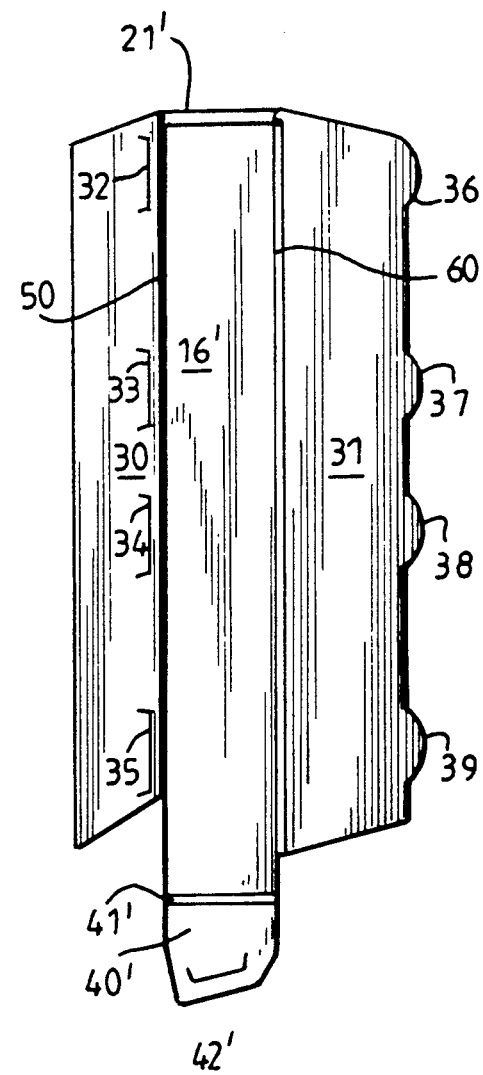

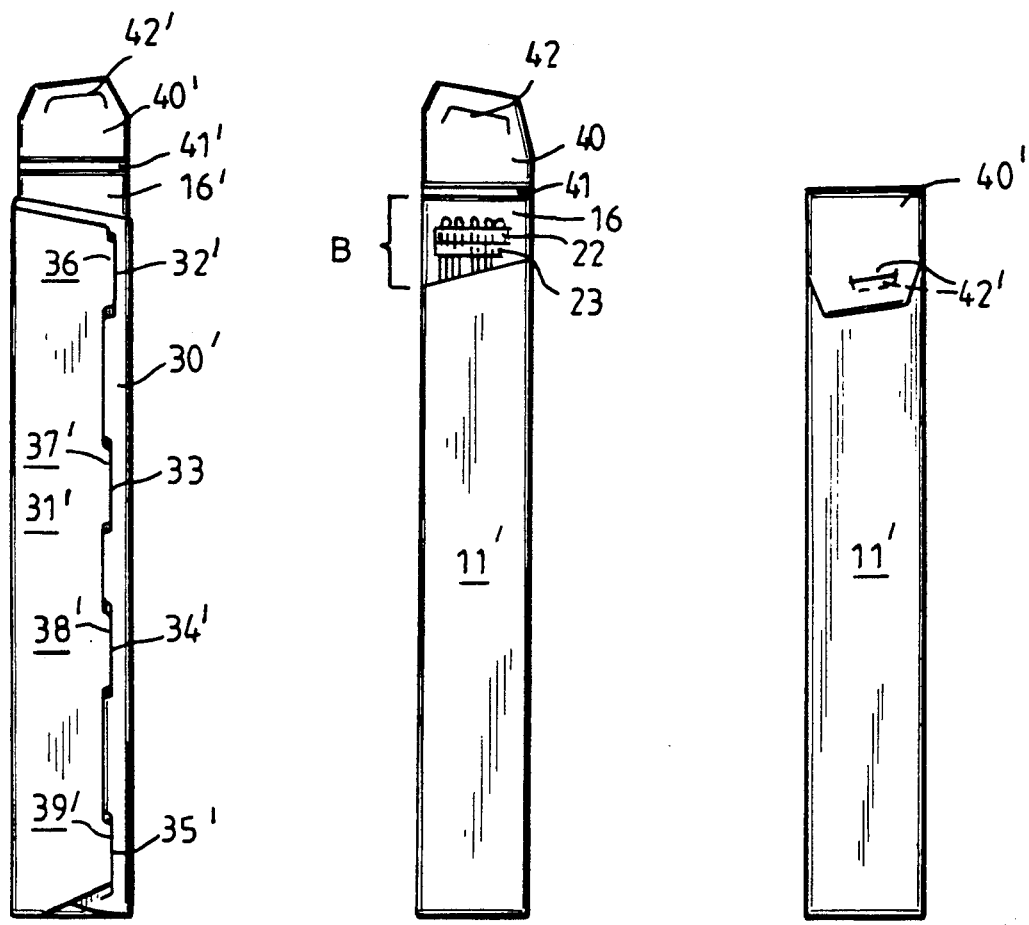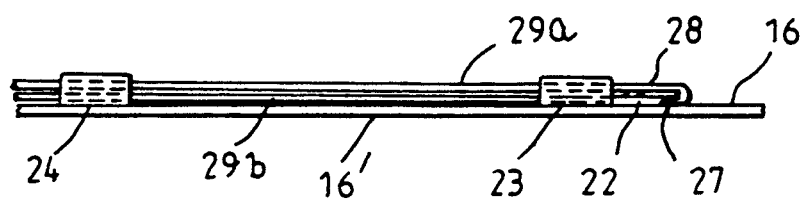

ARMED SUTURE PACKAGE

BACKGROUND OF THE INVENTION

This invention relates to a package for surgical sutures possessing needles affixed to at least one end thereof, i.e., "armed" sutures of the single needle and double needle types.

Packages for combined surgical suture-needle devices, or armed sutures, are constructed according to the nature of the devices and their intended use. There are many sizes of sutures and many materials of construction such as cotton, silk, stainless steel, and braided wire. There are also several types of needles including those of straight and curved configuration.

In general, suture packages for armed sutures are constructed with the objectives of providing safe and secure retention of their contents and ready removal of the sutures, either in a group or one at a time, with a minimum of handling. This requires that the suture be packaged in a manner which facilitates its ready accessibility and removal from the package and that once removed, the suture will exhibit little tendency to bend, kink or coil.

Various packaging arrangements are known for armed sutures, many of which are formed from a blank sheet of paperboard or other stiff material as described in U.S. Pat. Nos., 3,444,994; 3,985,227; 4,089,409; 4,120,395; 4,135,623; 4,533,041; 4,615,435; and, 4,896,767. For example, U.S. Pat. Nos. 3,985,227 and 4,135,623 each describes a suture package formed from a single sheet of stiff stock, such as 5-12 point solid bleached sulfate paperboard, which is subdivided into several panels, each panel having a particular function. The packages are specifically designed to accommodate a quantity of double armed sutures having relatively small needles mounted on polypropylene foam blocks, the suture strands being secured to polypropylene foam blocks having suture-receiving slits defined thereon.

SUMMARY OF THE INVENTION

In accordance with the present invention, there is provided a suture package for a quantity of armed sutures which comprises:

a) a cover panel defined by longitudinal sides and top and bottom transverse sides;

b) an armed suture-retaining panel defined by longitudinal sides and top and bottom transverse sides, the bottom transverse side of the armed suture-retaining panel being attached to the top transverse side of the cover panel, the length of the armed suture-retaining panel being greater than the length of the cover panel such that in the closed condition of the suture package, the cover panel will overlay less than the entire length of the armed suture-retaining panel thereby defining an open region for viewing and accessing the stored needles and their attached sutures;

c) needle-securing means attached to the armed suture-retaining panel at or near its top transverse side and within the open region thereof;

d) suture-securing means attached to the armed suture-retaining panel at one or more locations on said panel between the needle-securing means and its bottom transverse side;

e) first and second closure flaps, the first closure flap being attached to the cover panel along one longitudinal side thereof and the second closure flap being attached to the cover panel along the other longitudinal side thereof;

f) means for securing the first and second closure flaps in the closed condition of the suture package;

g) a third closure flap attached to the top transverse side of the armed suture-retaining panel, the length of the third closure flap being sufficient to cover the open region in the closed condition of the suture package; and, h) means for securing the third closure flap in the closed condition of the suture package.

The foregoing armed suture package provides safe and secure storage for a quantity of armed sutures. By opening the third, or top, closure flap, surgical personnel can readily view and access the stored sutures and remove one or more of them without opening the first and second closure flaps. The package can be made to accommodate a variety of armed suture configurations and if long enough, can store each suture with but a single bend along its length, an advantage which minimizes the need for subsequent handling of the removed armed suture.

BRIEF DESCRIPTION OF THE DRAWINGS

In the following drawings in which like reference numerals correspond to like elements and reference numerals bearing a prime (') mark correspond to the reverse side of the elements:

FIG. 1 is a plan view of an armed suture package of this invention in the fully open condition and loaded with a quantity of double armed sutures;

FIGS. 2-4 are plan views of the armed suture package of FIG. 1 at various stages of closure;

FIG. 5 is a plan view of the armed suture package of FIG. 1 in the fully closed condition; and FIG. 6 is an enlarged side elevation view of a portion of the armed suture-engaging panel of FIG. 1 illustrating the engagement of a surgical needle and its attached doubled-over suture strand to a series of polypropylene foam blocks.

DESCRIPTION OF THE PREFERRED EMBODIMENTS

As shown in FIG. 1, armed suture package 10 includes a cover panel 11 defined by longitudinal sides 12 and 13 and top and bottom transverse sides 14 and 15 and a somewhat lengthier armed suture-retaining panel 16 defined by longitudinal sides 17 and 18 and top and bottom transverse sides 19 and 20. Bottom transverse side 20 of armed suture-retaining panel 16 is attached to top transverse side 14 of cover panel 11, advantageously, through a narrow section 21 which allows for some expansion of the suture package in its loaded, closed condition.

A series of polyethylene foam blocks 22-26 are adhesively attached to the surface of armed suture-retaining panel 16, block 22 serving as a needle-securing member and blocks 23-26 with suture-receiving slits defined thereon serving as suture-securing members. As shown in FIG. 1 and the enlarged side elevation view of region A of FIG. 1 illustrated in FIG. 6, point 27 of a first needle 28 is made to a pierce foam block 22 thereby being securely and safely retained therein. The attached suture is doubled over to provide two strand portions 29a and 29b which are both retained within the suture-receiving slit of block 24. A second needle (not shown) is attached to the other end of the suture and is similarly made to pierce foam block 22 alongside first needle 28.

The remaining armed sutures in the package are similarly arranged on armed suture-receiving panel 16, each doubled-over suture occupying its own slit in each of foamed blocks 23-26.

Suture package 10 can be dimensioned to accommodate varying numbers and/or lengths of armed sutures. In one type of configuration, the package can accept up to six doubled-over, double armed sutures of from 15 to 30 inches in total length. Other configurations can, of course, be provided.

A first closure flap 30 is attached to cover panel 11 along longitudinal side 12 of the panel, preferably through a narrow section 50 which accommodates expansion of the suture package in its loaded, closed condition. Similarly, a second closure flap 31 is attached to cover panel 11 along the latter's longitudinal side 13, advantageously, through a narrow expansion section 60. In the closed condition of the first and second flaps, shown in FIG. 3, a series of die cut slits 32-35 defined on closure flap 30 engage corresponding tabs 36-39 to lock the flaps.

A third closure flap 40 is attached to top transverse side 19 of armed suture-retaining panel 16, advantageously, through a narrow section 41 which, like narrow section 21, allows for a moderate degree of expansion of the suture package in its loaded, closed condition. Diecut tab 42 is advantageously provided on third closure panel 40 to better secure the panel to cover panel 11' as shown in FIG. 5.

Loading of armed suture package 10 is advantageously carried out in a left-to-right direction. As shown in FIG. 1, the needle(s) of an individual suture is/are inserted in needle-securing foam block 22 and the suture is inserted into the corresponding slit of each of suture-retaining polyethylene foam blocks 23-26. The remaining armed sutures are similarly installed one by one on armed suture-retaining panel 16. Thereafter, as shown in FIG. 2, suture-retaining panel 16 is bent over upon cover panel 11 and in FIG. 3, the assembly is turned over and, if desired, rotated to the upright position whereupon closure flaps 30' and 31' are locked together. Again turning the assembly over as shown in FIG. 4, it is seen that an open region B is provided by the laying over of panel 16 on panel 11. This open region allows for ready viewing and removal of the armed sutures from package 10 without the need to open closure flaps 30 and 31. Finally, as shown in FIG. 5, closure flap 40 is tucked under cover panel 11' and locked in place employing tab 42.

What is claimed is:

1. An armed suture package which comprises:
   a) a cover panel defined by longitudinal sides and top and bottom transverse sides;
   b) an armed suture-retaining panel defined by longitudinal sides and top and bottom transverse sides, the bottom transverse side of the armed suture-retaining panel being attached to the top transverse side of the cover panel, the length of the armed suture-retaining panel being greater than the length of the cover panel such that in the closed condition of the suture package, the cover panel will overlay less than the entire length of the armed suture-retaining panel thereby defining an open region for viewing and accessing the stored needles and their attached sutures;
   c) needle-securing means attached to the armed suture-retaining panel at or near its top transverse side and within the open region thereof;
   d) suture-securing means attached to the armed suture-retaining panel at one or more locations on said panel between the needle-securing means and its bottom transverse side;
   e) first and second closure flaps, the first closure flap being attached to the cover panel along one longitudinal side thereof and the second closure flap being attached to the cover panel along the other longitudinal side thereof;
   f) means for securing the first and second closure flaps in the closed condition of the suture package;
   g) a third closure flap attached to the top transverse side of the armed suture-retaining panel, the length of the third closure flap being sufficient to cover the open region in the closed condition of the suture package; and,
   h) means for securing the third closure flap in the closed condition of the suture package.

2. The armed suture package of claim 1 wherein the armed suture-retaining panel is indirectly connected to the bottom transverse side of the cover panel through an expansion section which accommodates expansion of the package in its loaded and closed condition.

3. The armed suture package of claim 1 wherein the first and second closure flaps are indirectly connected to each longitudinal side of the cover panel through expansion sections which accommodate expansion of the package in its loaded and closed condition.

4. The armed suture package of claim 1 wherein the third closure panel is indirectly connected to the top transverse side of the suture-retaining panel through an expansion section which accommodates expansion of the package in its loaded and closed condition.

5. The armed suture package of claim 1 wherein the needle securing means is a block of foam material.

6. The armed suture package of claim 1 wherein the suture-retaining means is a block of foam material.

7. The armed suture package of claim 1 wherein the means for securing the first and second closure flaps in the closed condition of the suture package comprises slits on one of the flaps which can be made to cooperate in locking engagement with tabs on the other flap.

8. The armed suture of claim 1 wherein the means for securing the third closure flap in the closed condition of the suture package comprises a tab on the flap which engages an edge of the cover panel.

9. An armed suture package which comprises:
   a) a cover panel defined by longitudinal sides and top and bottom transverse sides;
   b) an armed suture-retaining panel defined by longitudinal sides and top and bottom transverse sides, the bottom transverse side of the armed suture-retaining panel being indirectly attached to the top transverse side of the cover panel through an expansion section which accommodates expansion of the package in its loaded and closed condition, the length of the armed suture-retaining panel being greater than the length of the cover panel such that in the closed condition of the suture package, the cover panel will overlay less than the entire length of the suture-retaining panel to define an open region for viewing and accessing the stored needles and their attached sutures;
   c) needle-securing means provided as a block of foam material attached to the armed suture-retaining panel at or near its top transverse side;
   d) suture-securing means provided as a block of foam material attached to the armed suture retaining panel at one or more locations on said panel between the needle securing means and its bottom transverse side;

e) first and second closure flaps, the first closure flap being indirectly attached to the cover panel along one longitudinal side thereof through an expansion section which accommodates expansion of the package in its loaded and closed condition and the second closure flap being indirectly attached to the cover panel along the other longitudinal side thereof through an expansion section which accommodates expansion of the package in its loaded and closed condition;

f) means for securing the first and second closure flaps in the closed condition of the suture package, said means comprising slits on one of the flaps which can be made to cooperate in locking engagement with tabs on the other flap;

g) a third closure flap indirectly attached to the top transverse side of the armed suture-retaining panel through an expansion section which accommodates the expansion of the suture package in its loaded and closed condition, the length of the third closure flap being sufficient to cover the open region in the closed condition of the suture package; and, h) means for securing the third closure flap in the closed condition of the suture package, said means comprising a tab on the flap which engages an edge of the cover panel.

10. The suture package of claim 9 accommodating up to six single or double armed sutures.

11. The suture package of claim 10 wherein the suture is a double armed suture possessing a single bend in the loaded condition of the package.

12. The suture package of claim 9 possessing at least two suture-retaining blocks of foam material.

* * * * *